United States Patent [19]
Aruga et al.

[11] Patent Number: 5,250,733
[45] Date of Patent: Oct. 5, 1993

[54] BENZYLIDENEINDENE COMPOUNDS AND ELECTROPHOTOGRAPHIC PHOTOCONDUCTOR USING THE SAME

[75] Inventors: Tamotsu Aruga, Numazu, Japan; Masaomi Sasaki, Susono; Mitsuru Hashimoto, Numazu, both of Japan

[73] Assignee: Ricoh Company, Ltd., Tokyo, Japan

[21] Appl. No.: 837,697

[22] Filed: Feb. 19, 1992

Related U.S. Application Data

[60] Continuation of Ser. No. 550,546, Jul. 10, 1990, abandoned, which is a division of Ser. No. 281,210, Dec. 8, 1988, Pat. No. 4,959,290.

[30] Foreign Application Priority Data

Dec. 8, 1987 [JP] Japan .................. 62-308597
Mar. 8, 1988 [JP] Japan .................. 63-054548

[51] Int. Cl.$^5$ .................. C07C 211/44; C07D 209/82
[52] U.S. Cl. .................. 564/308; 548/410; 548/411
[58] Field of Search .................. 548/410, 411, 445; 564/308, 309

[56] References Cited

FOREIGN PATENT DOCUMENTS 6306560 1/1988 Japan .

OTHER PUBLICATIONS

Bahner et al. "Anti cancer compounds . . . " J. Med. Chem. 16(4) 421-5 (1973).

*Primary Examiner*—C. Warren Ivy
*Assistant Examiner*—Celia Chang
*Attorney, Agent, or Firm*—Oblon, Spivak, McClelland, Maier & Neustadt

[57] ABSTRACT

Benzylideneindene compounds, which are useful not only as the photoconductive material for electrophotography, but also as a charge transporting material employed in a function-separating type photoconductor in which an organic or inorganic pigment is used as a charge generating material, and an electrophotographic photoconductor containing at least one of the above benzylideneindene compounds in a photoconductive layer thereof, are disclosed.

3 Claims, 10 Drawing Sheets

BENZYLIDENEINDENE COMPOUNDS AND ELECTROPHOTOGRAPHIC PHOTOCONDUCTOR USING THE SAME

This application is a continuation of application Ser. No. 07/550,546 filed on Jul. 10, 1990, now abandoned, which is a continuation of Ser. No. 07/281,210 filed Dec. 8, 1988, U.S. Pat. No. 4,959,290.

BACKGROUND OF THE INVENTION

The present invention relates to benzylideneindene compounds, and an electrophotographic photoconductor which comprises a photoconductive layer containing at least one of the benzylideneindene compounds.

Examples of photoconductive materials for use in the conventional photoconductors for use in electrophotography are inorganic materials such as selenium, cadmium sulfide and zinc oxide. In an electrophotographic process, a photoconductor is first exposed to corona charges in the dark, so that the surface of the photoconductor is electrically charged uniformly. The thus uniformly charged photoconductor is then exposed t original light images and the portions exposed to the original light images selectively become electroconductive so that electric charges dissipate from the exposed portions of the photoconductor, whereby latent electrostatic images corresponding to the original light images are formed on the surface of the photoconductor. The latent electrostatic images are then developed by the so-called toner which comprises a colorant, such as a dye or a pigment, and a binder agent made of a polymeric material; thus visible developed images can be obtained on the photoconductor.

Fundamental characteristics required of the photoconductor for use in electrophotography are: (1) chargeability to a predetermined potential in the dark; (2) minimum electric charge dissipation in the dark; and (3) quick dissipation of electric charges upon exposure to light.

While the above-mentioned inorganic photoconductive materials have many advantages over other conventional photoconductive materials, they also have several shortcomings.

For example, a selenium photoconductor, which is widely used at present and sufficiently meets the above-mentioned requirements (1) to (3), has the shortcomings that its production conditions are difficult and, accordingly, its production cost is high. Further it is difficult to work it into the form of a belt due to its poor flexibility, and it is so vulnerable to heat and mechanical shock that it must be handled with the utmost care.

Cadmium sulfide photoconductors and zinc oxide photoconductors are prepared by dispersing cadmium sulfide or zinc oxide in a binder resin. Therefore they are so poor in mechanical properties such as surface smoothness, hardness, tensile strength and wear resistance that they are not suitable as photoconductors for use in plain paper copiers in which the photoconductors are used in quick repetition.

Recently, varieties of the organic electrophotographic photoconductor have been proposed to cover the shortcomings of the inorganic photoconductor, and some of them are in fact put to practical use. Representative examples of the organic electrophotographic photoconductor are an electrophotographic photoconductor comprising poly-N-vinylcarbazole and 2,4,7-trinitrofluorene-9-on (U.S. Pat. No. 3,484,237), a photoconductor in which poly-N-vinylcarbazole is sensitized by a pyrylium salt type dyestuff (Japanese Patent Publication 48-25658), a photoconductor containing as the main component an organic pigment (Japanese Laid-Open Patent Application 47-37543), and a photoconductor containing as the main component an eutectic crystalline complex made of a dye and a resin (Japanese Laid-Open Patent Application 47-10735).

Although the above-mentioned organic electrophotographic photoconductors have many superiorities for practical use compared with other conventional photoconductors, they do still not satisfy all the requirements of the electrophotographic photoconductor.

The previously mentioned electrophotographic photoconductors, which are different in the application and the preparation method thereof, can generally show excellent properties when the superior electroconductive material is used.

SUMMARY OF THE INVENTION

It is therefore a first object of the present invention to provide benzylideneindene compounds which can satisfy all the necessary fundamental electrophotographic characteristics and are advantageous as a photoconductive material contained in a photoconductive layer of an electrophotographic photoconductor.

Another object of the present invention is to provide an improved electrophotographic photoconductor, from which the above-mentioned conventional shortcomings are eliminated. More specifically, it is an object of the present invention to provide an electrophotographic photoconductor which is manufactured without difficulty at relatively low cost and has good durability.

The above first object of the present invention can be attained by benzylideneindene compounds having the following formula (I):

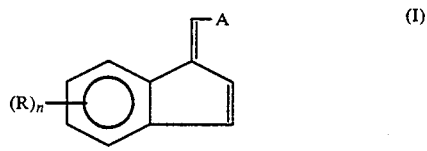

(I)

wherein A represents a N-substituted carbazolyl group or

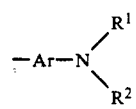

wherein Ar represents an aromatic hydrocarbon group or a heterocyclic group; and $R^1$ and $R^2$ each represent a substituted or unsubstituted alkyl group, or a substituted or unsubstituted aryl group;

R represents an alkyl group, an alkoxyl group or a halogen; and n is an integer of 0 to 4, and when n is 2, 3 or 4, Rs may be the same or different.

Of the above benzylideneindene compounds of the formula (I), the following benzylideneindene compounds of formula (I-1) may also be preferably employed:

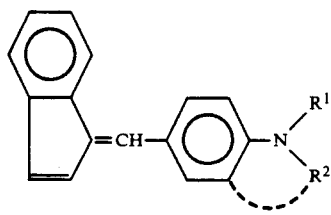

(I-1)

wherein $R^1$ and $R^2$ each represent an alkyl group having 1 to 4 carbon atoms, a phenyl group which may have a substituent, a benzyl group which may have a substituent, or a biphenylyl group, and $R^1$ or $R^2$ may form a ring in combination of the benzene ring in the above formula as indicated by the broken line.

Another object of the present invention can be attained by an electrophotographic photoconductor in which a photoconductive layer is overlaid on an electroconductive support, which photoconductive layer comprises as an effective component at least one benzylideneindene compound of the above formula (I).

DETAILED DESCRIPTION OF THE PREFERRED EMBODIMENTS

Figure 1:
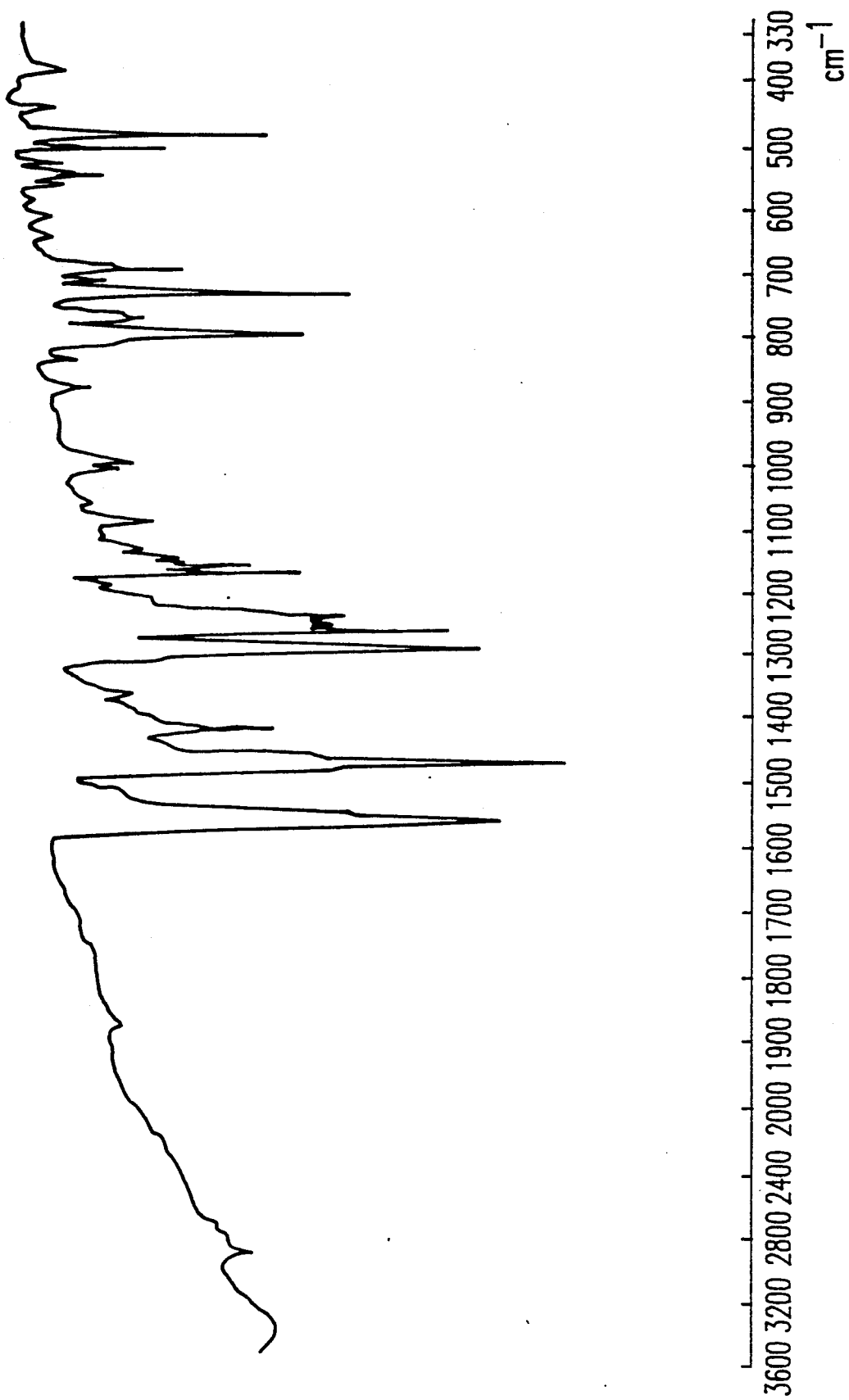
FIG. 1 to FIG. 9 are graphs showing the infrared absorption spectra of benzylideneindene compounds obtained in Synthesis Examples 1 to 9.

In the above-mentioned general formula (I), the N-substituted carbazolyl group represented by A has a formula of

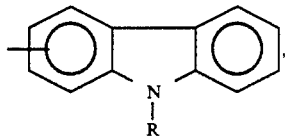

wherein R may be selected from the group consisting of an alkyl group having 1 to 4 carbon atoms, and a phenyl group which may have a substituent, selected from the group consisting of an alkyl group having 1 to 4 carbon atoms and an alkoxyl group having 1 to 4 carbon atoms.

In the above-mentioned formula I), the aromatic hydrocarbon group represented by Ar may be selected from the group consisting of a phenyl group which may have a substituent, a naphthylene group which may have a substituent, and a biphenylene group. The heterocyclic group which is also represented by Ar may be

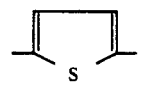

In the above-mentioned formula (I), the alkyl group represented by $R^1$ or $R^2$ has 1 to 4 carbon atoms. The aryl group which is also represented by $R^1$ or $R^2$ may be selected from the group consisting of a phenyl group, a benzyl group and a biphenylyl group, which may have a substituent selected from the group consisting of an alkyl group having 1 to 4 carbon atoms, an alkoxyl group having 1 to 4 carbon atoms and a halogen.

In the above-mentioned formula (I-1), the substituent of the benzyl group represented by $R^1$ or $R^2$ may be an alkyl group having 1 to 4 carbon atoms. The substituent of the phenyl group which is also represented by $R^1$ or $R^2$ may be selected from the group consisting of an alkyl group having 1 to 4 carbon atoms, an alkoxyl group having 1 to 4 carbon atoms and a halogen.

Specific examples of the benzylideneindene compounds having the formula (I) according to the present invention are as follows:

TABLE 1

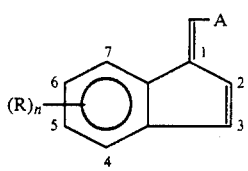

| Benzylideneindene Compound No. | A | $(R)_n$ |
|---|---|---|
| 1 | 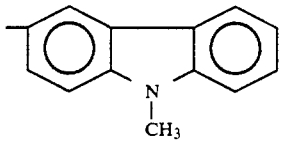 | n = 0 |
| 2 | 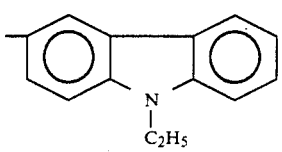 | n = 0 |

TABLE 1-continued
| | | |
|---|---|---|
| 3 | 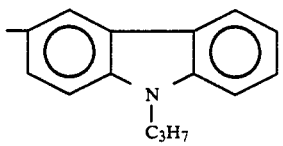 | 4-CH₃ |
| 4 | 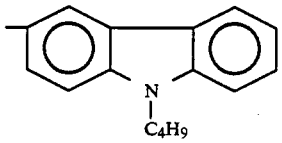 | n = 0 |
| 5 | 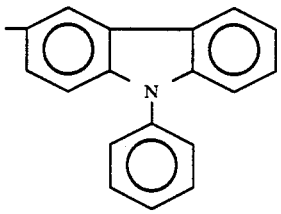 | n = 0 |
| 6 | 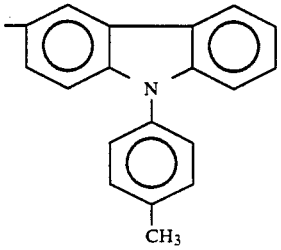 | 5-OCH₃ |
| 7 | 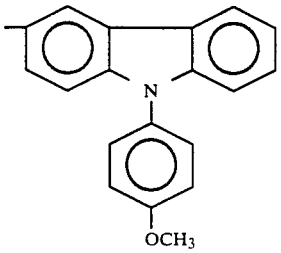 | n = 0 |
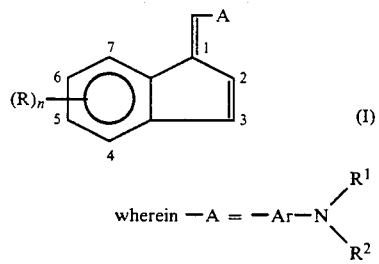
wherein $-A = -Ar-N\begin{matrix}R^1\\R^2\end{matrix}$
| Benzylideneindene | A | | | |
|---|---|---|---|---|
| Compound No. | Ar | $R^1$ | $R^2$ | $(R)_n$ |
| 8 | ⌬ (para) | —CH₃ | —CH₃ | n = 0 |
| 9 | " | —CH₃ | ⌬ | n = 0 |

TABLE 1-continued
| No. | | 7 | 8 | |
|---|---|---|---|---|
| 10 | " | —C₂H₅ | —C₂H₅ | n = 0 |
| 11 | " | —C₂H₅ |  | n = 0 |
| 12 | " |  |  | n = 0 |
| 13 | " | 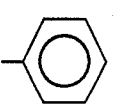 | 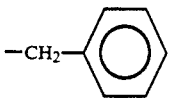 | n = 0 |
| 14 | " | 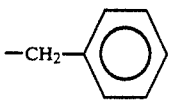 | 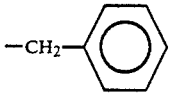 | 5-CH₃ |
| 15 | " | 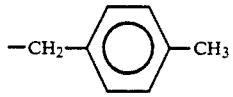 | 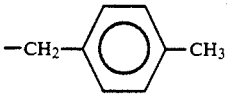 | n = 0 |
| 16 | " | 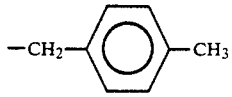 | —CH₃ | 6-CH₃ |
| 17 | " | 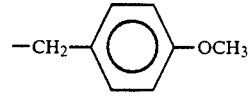 | 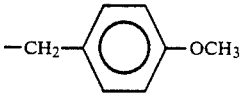 | 7-CH₃ |
| 18 | " | 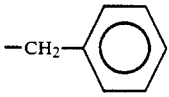 |  | n = 0 |
| 19 | " | 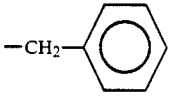 | 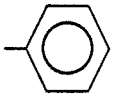 | n = 0 |
| 20 | " | 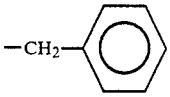 | 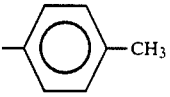 | n = 0 |
| 21 | 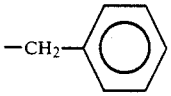 | 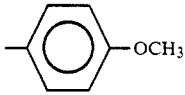 | 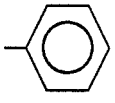 | 6-OCH₃ |
| 22 | " |  |  | n = 0 |
| 22-1 | " | 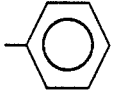 | 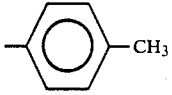 | n = 0 |

TABLE 1-continued
| | | | | |
|---|---|---|---|---|
| 23 | " | 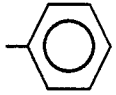 | 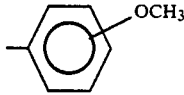 | n = 0 |
| 24 | " | 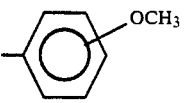 |  | n = 0 |
| 25 | " | 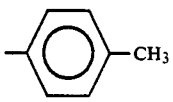 | 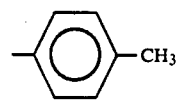 | 5-OCH$_3$ |
| 26 | " | 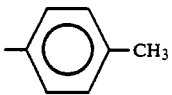 | 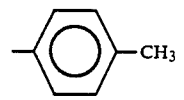 | 6-OCH$_3$ |
| 27 | " | 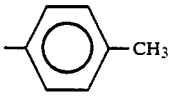 | 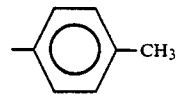 | 4.5-(CH$_3$)$_2$<br>7-OCH$_3$ |
| 28 | " | 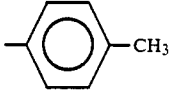 | 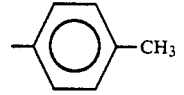 | 4.7-(CH$_3$)$_2$ |
| 29 | " | 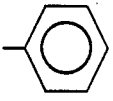 | 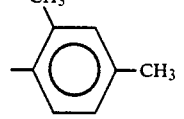 | 4.7-(CH$_3$)$_2$ |
| 30 | " | 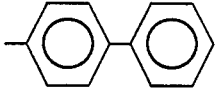 | 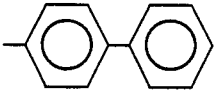 | n = 0 |
| 31 | " | 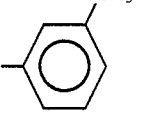 | 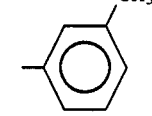 | n = 0 |
| 32 | " | 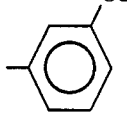 | 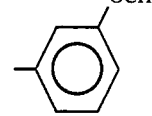 | n = 0 |
| 33 | 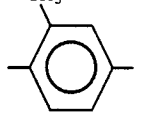 | 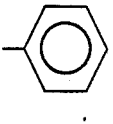 | 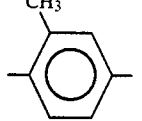 | n = 0 |
| 34 | 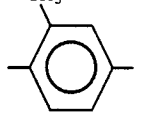 | —CH$_3$ | —CH$_3$ | 4.5-(CH$_3$)$_2$<br>7-OCH$_3$ |

TABLE 1-continued
| | 11 | 12 | | |
|---|---|---|---|---|
| 35 | " | 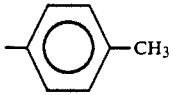 | 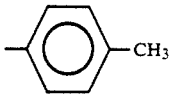 | 6-Br 4,7-(CH₃)₂ |
| 36 | " |  | 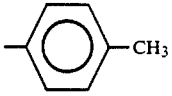 | n = 0 |
| 37 | " | 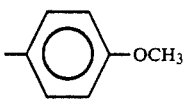 | 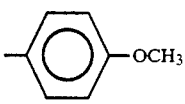 | n = 0 |
| 38 | " |  | 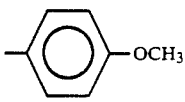 | n = 0 |
| 39 | " |  | 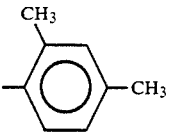 | n = 0 |
| 40 | " | —CH₂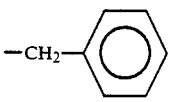 | 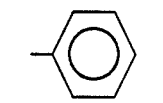 | n = 0 |
| 41 | " | —CH₂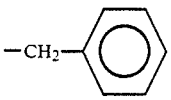 | —CH₂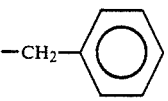 | n = 0 |
| 42 | " | 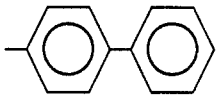 | 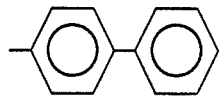 | n = 0 |
| 43 | 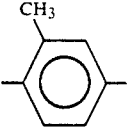 | 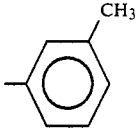 | 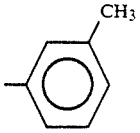 | n = 0 |
| 44 | 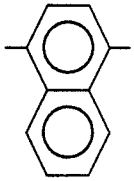 | —CH₃ | —CH₃ | n = 0 |
| 45 | " | —CH₃ | 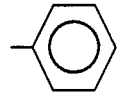 | n = 0 |
| 46 | " | —CH₂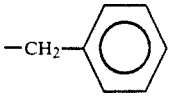 | —CH₂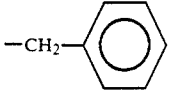 | n = 0 |

TABLE 1-continued

| No. | Ar | R1 | R2 | n |
|---|---|---|---|---|
| 47 | " | -CH₂-C₆H₅ | -C₆H₅ | n = 0 |
| 48 | " | -C₆H₅ | -C₆H₅ | n = 0 |
| 49 | " | -C₆H₄-CH₃ (p) | -C₆H₅ | n = 0 |
| 50 | " | -C₆H₄-CH₃ (p) | -C₆H₄-CH₃ (p) | n = 0 |
| 51 | " | -C₆H₄-OCH₃ (p) | -C₆H₄-OCH₃ (p) | n = 0 |
| 52 | " | -C₆H₄-OCH₃ (o) | -C₆H₅ | n = 0 |
| 53 | " | -C₆H₅ | -C₆H₃(CH₃)₂ (2,4) | n = 0 |
| 54 | " | -C₆H₄-C₆H₅ (p) | -C₆H₄-C₆H₅ (p) | n = 0 |
| 55 | " | -C₆H₄-CH₃ (m) | -C₆H₄-CH₃ (m) | n = 0 |
| 56 | naphthyl | -C₆H₄-OCH₃ (m) | -C₆H₄-OCH₃ (m) | n = 0 |
| 57 | thienyl | -CH₃ | -CH₃ | n = 0 |
| 58 | " | -CH₃ | -C₆H₅ | n = 0 |
| 59 | " | -C₆H₅ | -CH₂-C₆H₅ | n = 0 |

TABLE 1-continued

| | | | | |
|---|---|---|---|---|
| 60 | " | —CH₂—C₆H₅ | —CH₂—C₆H₅ | n = 0 |
| 61 | " | —C₆H₅ | —C₆H₅ | n = 0 |
| 62 | " | —C₆H₅ | —C₆H₄—CH₃ | n = 0 |
| 63 | " | —C₆H₄—CH₃ | —C₆H₄—CH₃ | n = 0 |
| 64 | " | —C₆H₅ | —C₆H₄—OCH₃ | 5-CH₃ |
| 65 | " | —C₆H₄—OCH₃ | —C₆H₄—OCH₃ | n = 0 |
| 66 | " | —C₆H₅ | —C₆H₃(CH₃)₂ | n = 0 |
| 67 | " | —C₆H₄—C₆H₅ | —C₆H₄—C₆H₅ | n = 0 |
| 68 | " | —C₆H₄—OCH₃ | —C₆H₄—OCH₃ | n = 0 |
| 69 | naphthyl | —CH₃ | —CH₃ | n = 0 |
| 70 | " | —CH₃ | —C₆H₅ | n = 0 |
| 71 | " | —C₆H₅ | —CH₂—C₆H₅ | n = 0 |

TABLE 1-continued

| # | 17 | (middle) | 18 | (right) |
|---|---|---|---|---|
| 72 | " | —CH₂—Ph | —CH₂—Ph | n = 0 |
| 73 | " | —Ph | —Ph | n = 0 |
| 74 | " | —C₆H₄—CH₃ (p) | —Ph | 6-OCH₃ |
| 75 | " | —C₆H₄—CH₃ (p) | —C₆H₄—CH₃ (p) | n = 0 |
| 76 | " | —C₆H₄—CH₃ (m) | —C₆H₄—CH₃ (m) | n = 0 |
| 77 | " | —C₆H₄—OCH₃ (p) | —Ph | n = 0 |
| 78 | " | —C₆H₄—OCH₃ (p) | —C₆H₄—OCH₃ (p) | n = 0 |
| 79 | " | —C₆H₄—OCH₃ (m) | —C₆H₄—OCH₃ (m) | n = 0 |
| 80 | " | —Ph | —C₆H₃(CH₃)₂ | n = 0 |
| 81 | " | —C₆H₄—C₆H₅ | —C₆H₄—C₆H₅ | n = 0 |
| 82 | —C₆H₄—C₆H₄— | —C₆H₄—CH₃ | —C₆H₄—CH₃ | n = 0 |
| 83 | —C₆H₄—C₆H₄— | —C₆H₄—OCH₃ | —C₆H₄—OCH₃ | n = 0 |
| 84 | —C₆H₄— | —Ph | —C₆H₄—CH₃ | n = 0 |

TABLE 1-continued

| | | | | |
|---|---|---|---|---|
| 85 | " | " |  | n = 0 |

The benzylideneindene compounds having the formula (I) according to the present invention can be prepared by the method described in C. T. Bahner, H. Kinder, D. Brotherton, J. Spiggle and L. Gutman J. Med Chem., 390 (1965). More specifically, the benzylideneindene compounds having the formula (I) according to the present invention can be prepared by allowing indene or an indene derivative (IIa) to react with an aldehyde compound having the following formula (IIb) in the presence of a basic catalyst with the reaction temperature set in the range of room temperature to about 100° C.

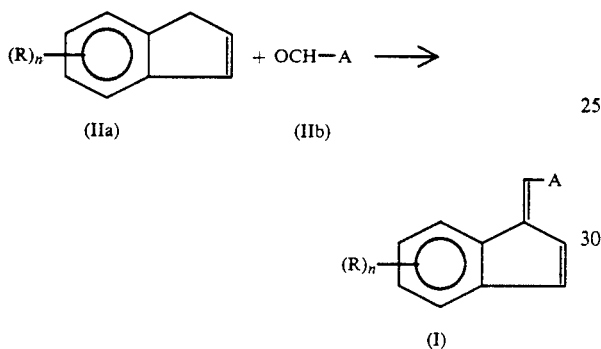

wherein A and R are the same as previously defined.

Specific examples of the basic catalyst for the above reaction are sodium hydroxide, potassium hydroxide, lithium methoxide and sodium methoxide.

Specific examples of the reaction solvent are methanol, ethanol, isopropanol, butanol, 2-methoxyethanol, 1,2-dimethoxyethane, bis(2-methoxyethyl)ether, dioxane, tetrahydrofuran, toluene, xylene, dimethyl sulfoxide, N,N-dimethylformamide, N-methylpyrrolidone and 1,3-dimethyl-2-imidazolidone.

The reaction temperature for the above reaction can be set in a relatively wide range, depending on (1) the stability of the solvent employed in the presence of the basic catalyst, (2) the reactivities of the condensation components, that is, the compound of the formula (II) and indene, and (3) the reactivity of the basic catalyst in the solvent employed, which catalyst works as a condensation agent in this reaction.

When a polar solvent is, for example, employed as the reaction solvent, the reaction temperature can be set in the range of room temperature to about 100° C., preferably in the range of room temperature to about 80° C. However, if it is desired to shorten the reaction time or when a less reactive condensation agent is employed, the reaction temperature can be elevated beyond the aforementioned range.

The benzylideneindene compounds according to the present invention are remarkably useful for the electrophotographic photoconductor as the photoconductive materials. These benzylideneindene compounds can be either optically and chemically sensitized by a sensitizer such as dyes and Lewis acids. Furthermore, the above-mentioned benzylideneindene compounds are particularly useful as a charge transporting material employed in the so-called function-separating type photoconductor which uses an organic or inorganic pigment as a charge generating material.

The present invention will now be explained in detail by referring to the following synthesis examples of the benzylideneindene compounds.

SYNTHESIS EXAMPLE 1

Synthesis of Benzylideneindene Compound No. 22-1 in Table-1

A mixture of 1.31 g of indene and 3.01 g of 4-[N,N-bis(4-tolyl)amino]benzaldehyde was added to 50 ml of absolute ethanol. The mixture was refluxed under application of heat in a stream of a nitrogen gas, with 15 ml of an absolute ethanol solution of potassium hydroxide being gradually added dropwise. After the completion of the dropwise addition of the ethanol solution, refluxing was further continued for 25 minutes under application of heat. The thus obtained reaction mixture was cooled to room temperature, and poured into 150 ml of water. The mixture was extracted with toluene. A toluene layer was separated from the mixture, and dried by use of magnesium sulfide. The toluene was removed from the toluene solution to obtain an extract. The extract was subjected to chromatography using silica gel as a carrier and toluene/n-hexane with the mixing ratio of 1:1 as an eluting solution. This extract was recrystallized from a mixed solvent of ethyl acetate and ethanol, whereby 127 g of 1-{4-[N,N-bis(4-tolyl)amino]benzylidene}indene, which is given as benzylideneindene compound No. 22-1 according to the present invention in Table 1, was obtained in the form of orange needles in a 32% yield. The melting point of the product was 178.5° C. to 179.5° C.

The results of the elemental analysis of the thus obtained benzylideneindene compound No. 22-1 were as follows:

| | % C | % H | % N |
|---|---|---|---|
| Calculated | 90.28 | 6.23 | 3.47 |
| Found | 90.19 | 6.31 | 3.51 |

The above calculation was based on the formula for benzylideneindene compound No. 22 of $C_{30}H_{25}N$.

An infrared absorption spectrum of the above benzylideneindene compound No. 22-1, taken by use of a KBr tablet, is shown in FIG. 1.

SYNTHESIS EXAMPLES 2 TO 9

Synthesis Example 1 was repeated except that 4-[N,N-bis(4-tolyl)amino[benzaldehyde employed in Synthesis Example 1 was replaced by the aldehyde compounds No. 2 to No. 9 as shown in the following Table 2, whereby benzylideneindene compounds according to the present invention were obtained.

The melting points and the results of the elemental analysis of the thus obtained benzylideneindene compounds are shown in Table 3.

Infrared absorption spectra of the above benzylideneindene compounds, taken by use of a KBr tablet, are shown in FIGS. 2 to 9.

TABLE 2

| Synthesis Example No. | Aldehyde Compound | Benzylideneindene Compound |
|---|---|---|
| 1 | | |
| 2 | | |
| 3 | | |
| 4 | | |
| 5 | | |
| 6 | | |

TABLE 2-continued

| Synthesis Example No. | Aldehyde Compound | Benzylideneindene Compound |
|---|---|---|
| 7 | | |
| 8 | | |
| 9 | | |

TABLE 3

| Synthesis Example No. | Melting Point (°C.) | Results of Elemental Analysis (%) Found/Calculated | | |
|---|---|---|---|---|
| | | C | H | N |
| 1 | 178.0 ~ 178.5 | 90.28/90.19 | 6.23/6.31 | 3.47/3.51 |
| 2 | 139.0 ~ 140.0 | 90.60/90.53 | 5.72/5.70 | 3.77/3.77 |
| 3 | 107.5 ~ 108.0 | 90.20/90.35 | 5.87/6.01 | 3.57/3.63 |
| 4 | 92.5 ~ 94.0 | 89.41/89.28 | 6.07/6.19 | 4.40/4.53 |
| 5 | 122.0 ~ 123.0 | 86.83/86.75 | 5.53/5.77 | 3.42/3.49 |
| 6 | 148.0 ~ 149.0 | 83.43/83.50 | 5.68/5.84 | 3.26/3.25 |
| 7 | 113.5 ~ 115.0 | 82.89/82.85 | 4.84/4.97 | 3.55/3.45 |
| 8 | 159.0 ~ 160.5 | 90.11/90.19 | 6.51/6.31 | 3.41/3.51 |
| 9 | 104.5 ~ 106.0 | 89.75/89.68 | 5.70/5.96 | 4.20/4.36 |

In the photoconductor according to the present invention, at least one benzylideneindene compound having the formula (I) is contained in the photoconductive layer 2, 2a or 2b. The benzylideneindene compounds an be employed in different ways, for example, as shown in FIG. 1, FIG. 2 and FIG. 3.

In the photoconductor as shown in FIG. 1, a photoconductive layer 2 is formed on an electroconductive support 1, which photoconductive layer 2 comprises a benzylideneindene compound, a sensitizing dye and a binder agent (binder resin). In this photoconductor, the benzylideneindene compound works as a photoconductive material, through which charge carriers which are necessary for the light decay of the photoconductor are generated and transported. However, the benzylideneindene compound itself scarcely absorbs light in the visible light range and, therefore, it is necessary to add a sensitizing dye which absorbs light in the visible light range in order to form latent electrostatic images by use of visible light.

Figure 2:
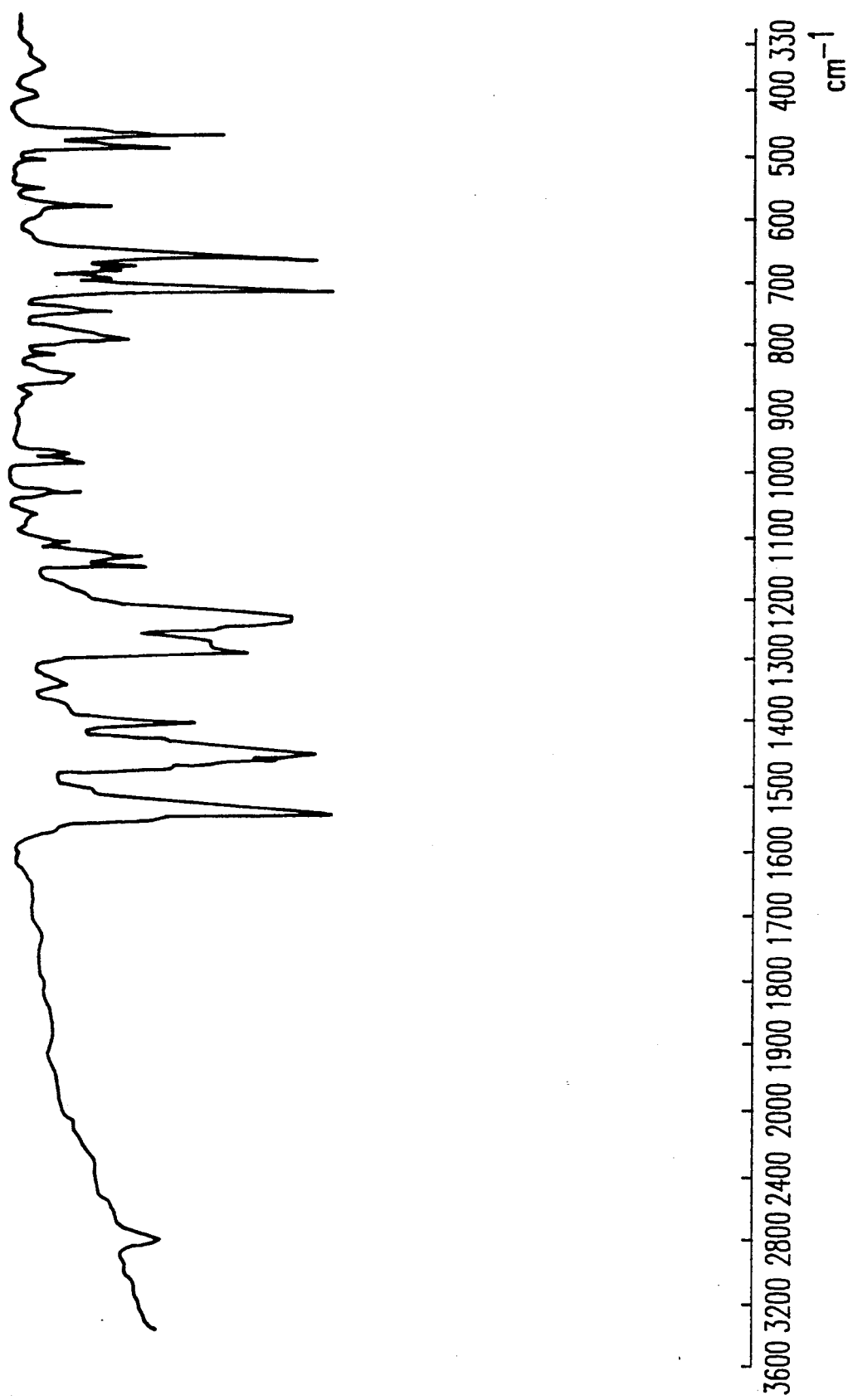
Figure 3:
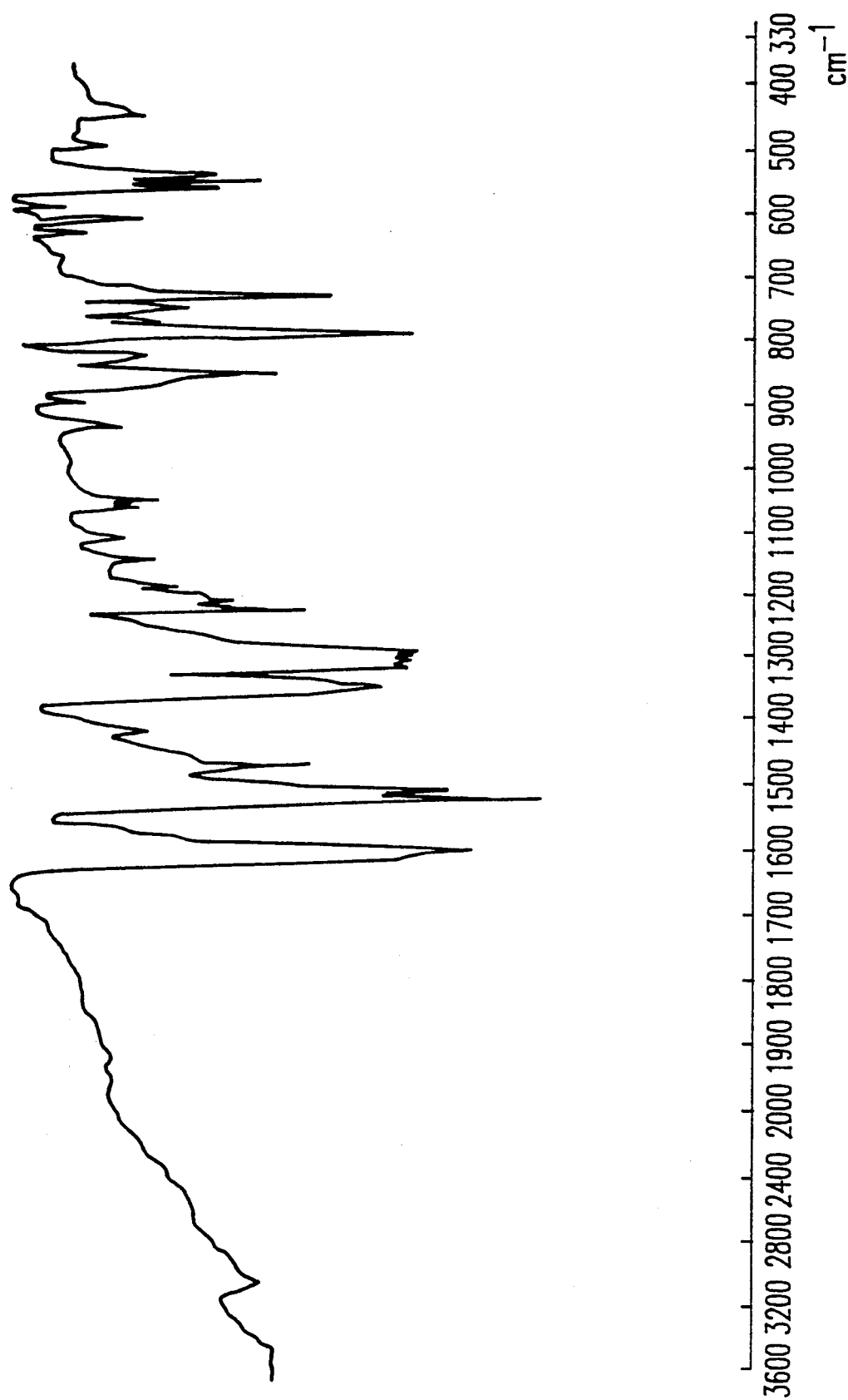
Figure 4:
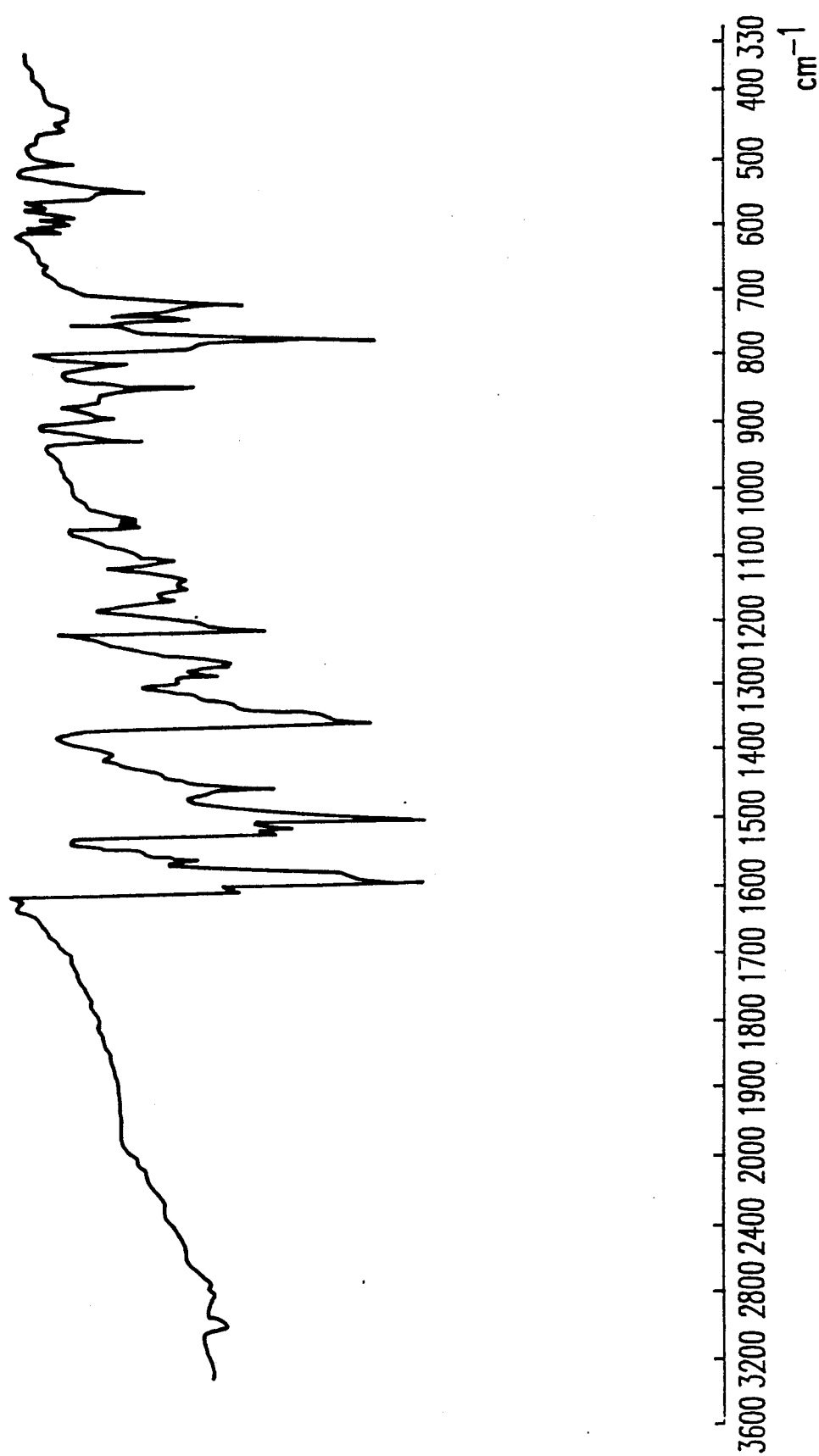
Figure 5:
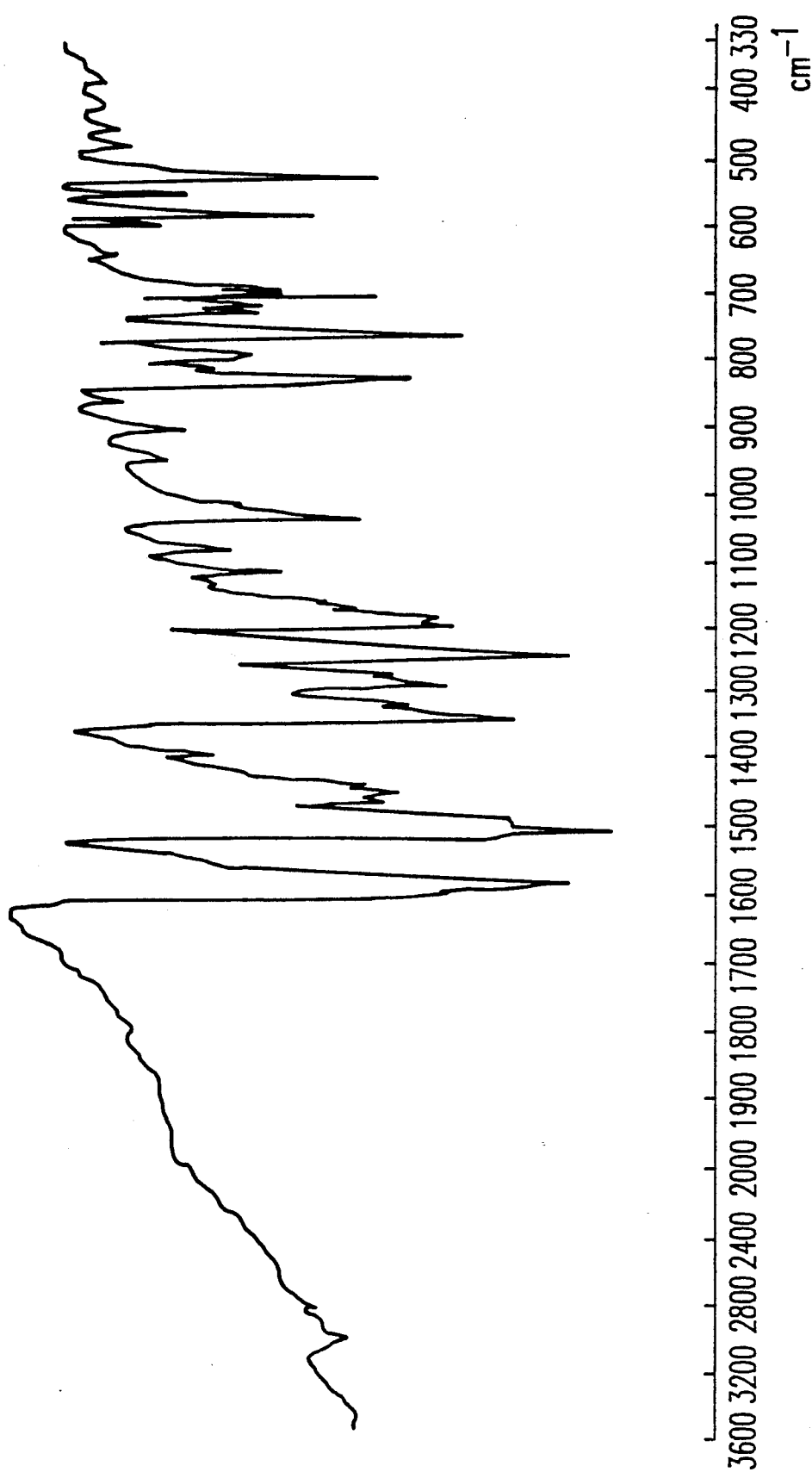
Figure 6:
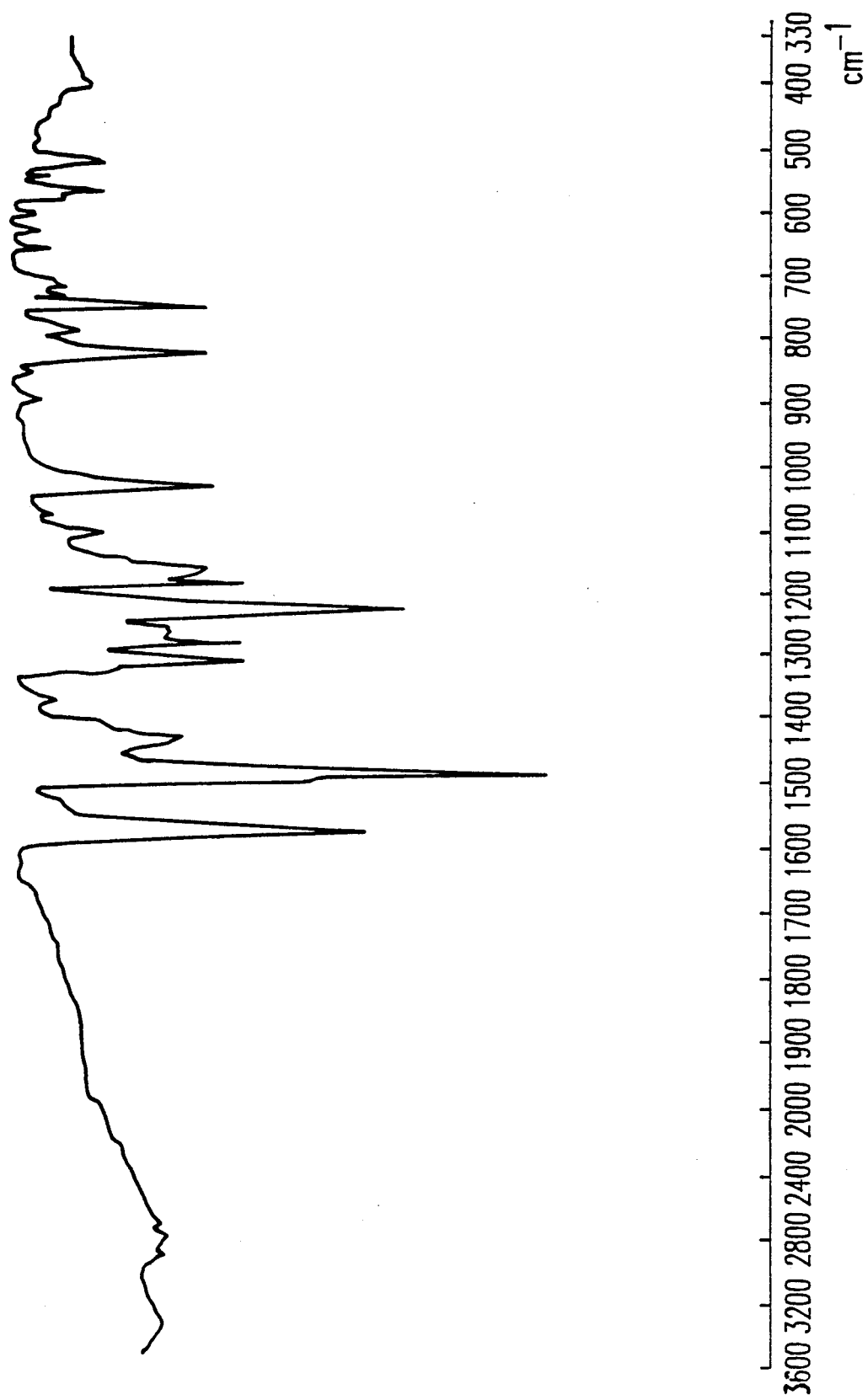
Figure 7:
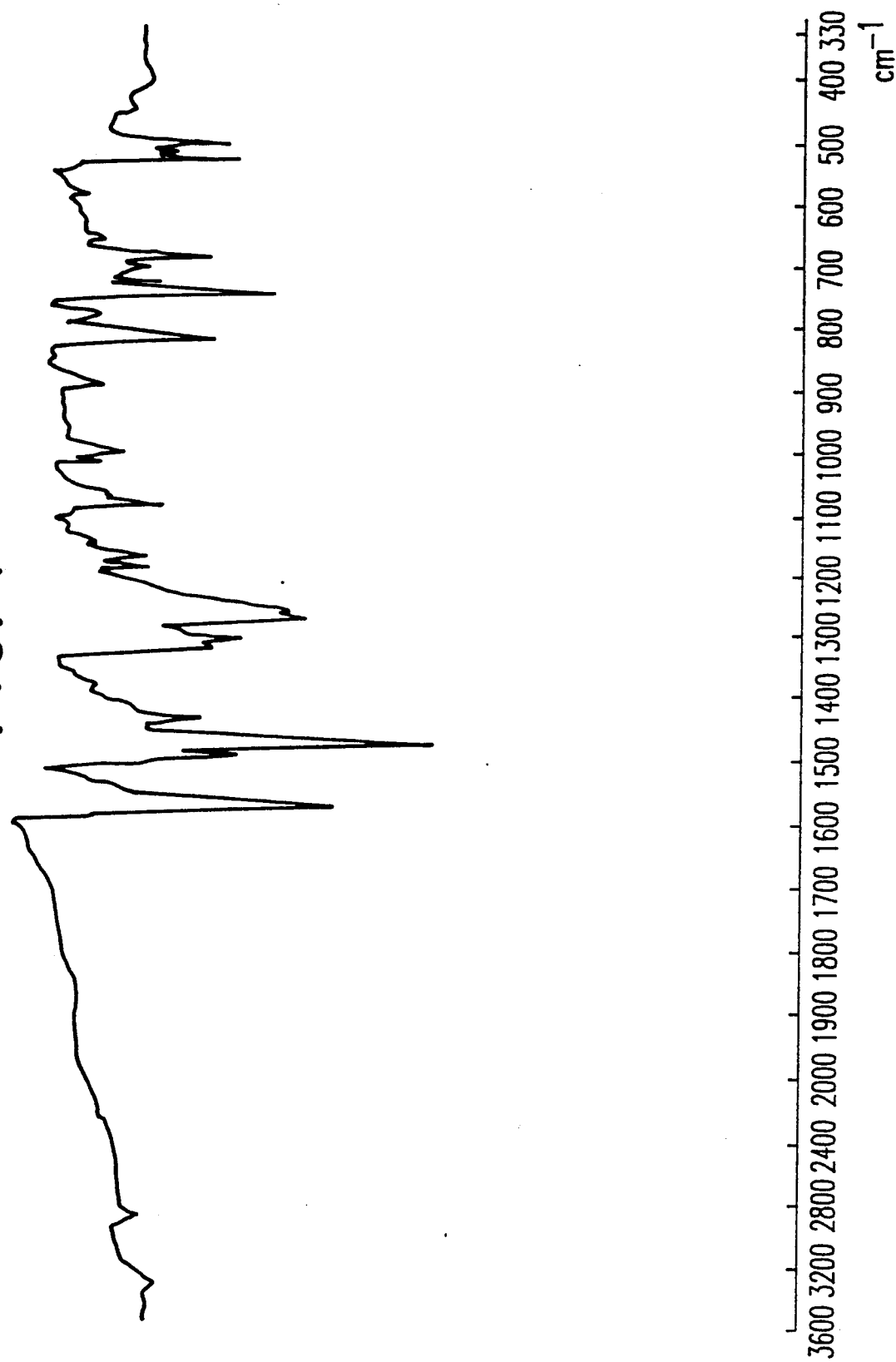
Figure 8:
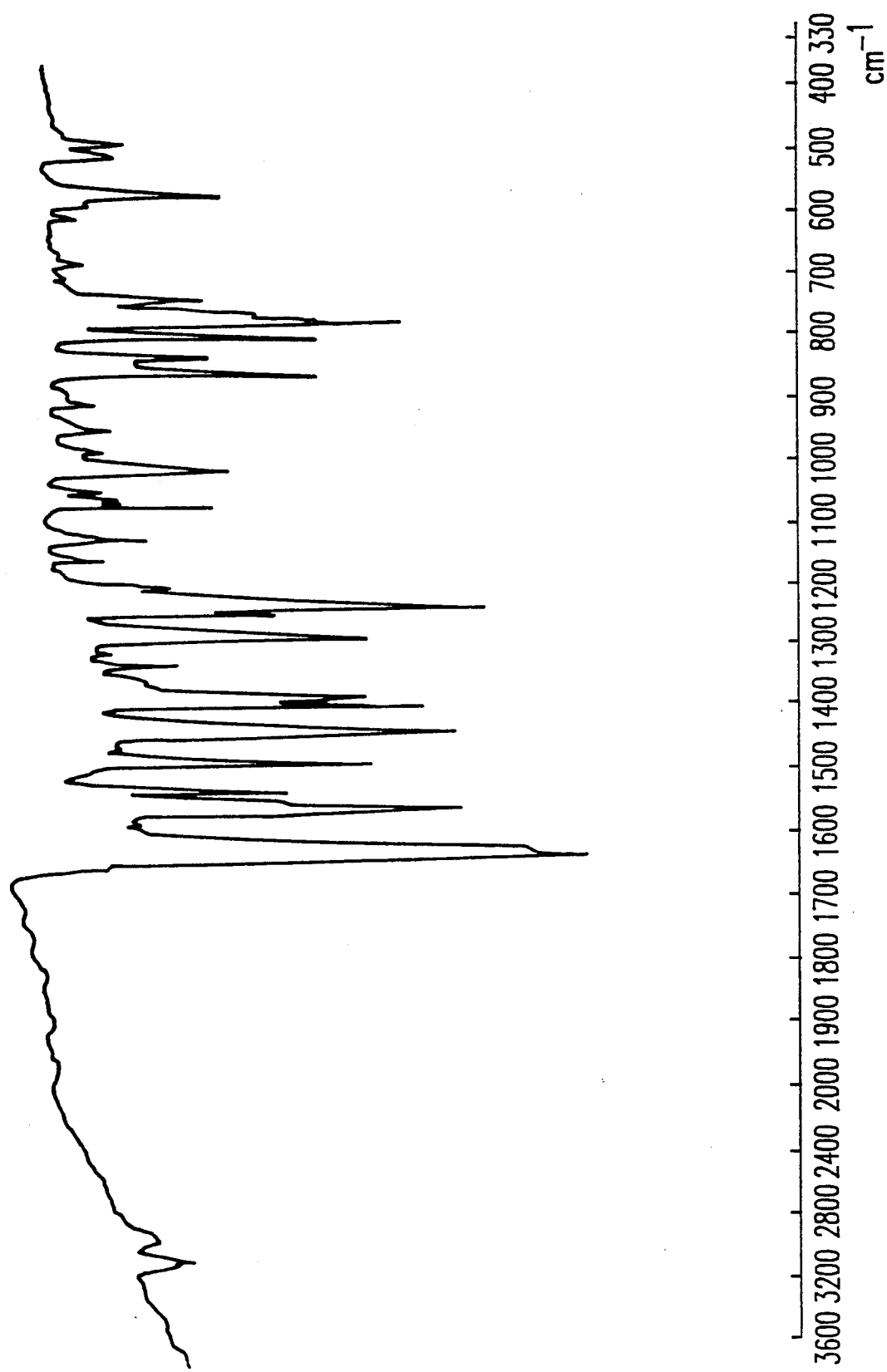
Figure 9:
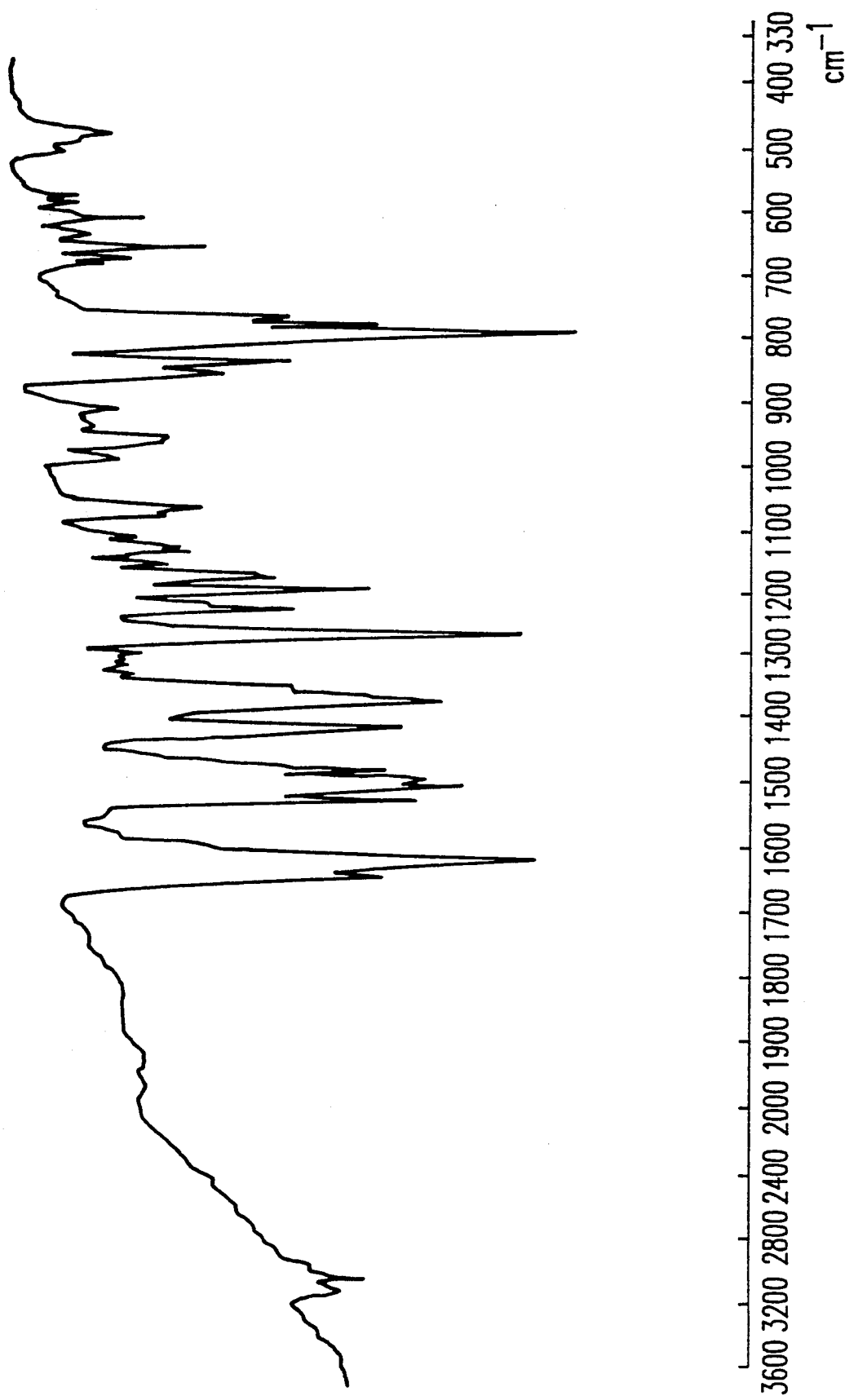
Figure 10:
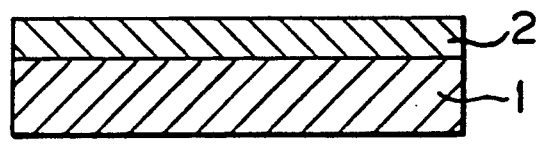
FIG. 10 is a schematic cross-sectional view of an embodiment of an electrophotographic photoconductor according to the present invention.
Figure 11:
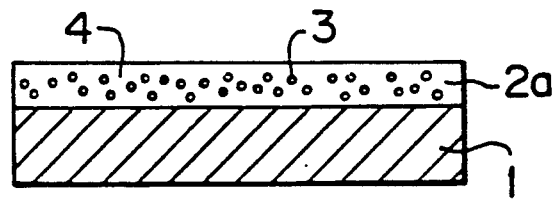
FIG. 11 is a schematic cross-sectional view of another embodiment of an electrophotographic photoconductor according to the present invention.
Figure 12:
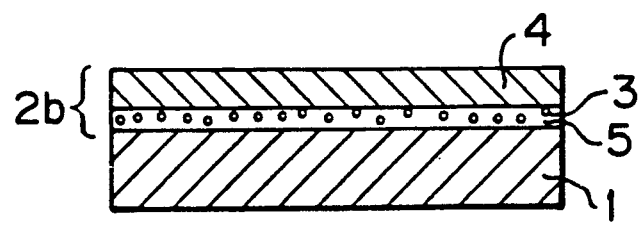
FIG. 12 is a schematic cross-sectional view of a further embodiment of an electrophotographic photoconductor according to the present invention.

In the photoconductor as shown in FIG. 2, a photoconductive layer 2a is formed on an electroconductive support 1, which photoconductive layer 2a comprises a charge generating material 3 dispersed in a charge transporting medium 4 comprising a benzylideneindene compound and a binder agent. In this embodiment, the benzylideneindene compound and the binder agent (or the mixture of a binder agent and a plasticizer) constitute the charge transporting medium 4 in combination. The charge generating material 3 which is, for example, an inorganic or organic pigment, generates charge carriers. The charge transporting medium 4 accepts the charge carriers generated by the charge generating material 3 and transports those charge carriers.

In this electrophotographic photoconductor, it is basically necessary that the light-absorption wavelength regions of the charge generating material 3 and the benzylideneindene compound according to the present invention not overlap in the visible light range. This is because it is necessary that light pass through the surface of the charge material 3 in order that the charge generating material 3 produce charge carrier efficiently. Since the benzylideneindene compounds according to the present invention having the above-described general formula (I) do not substantially absorb light in the visible range, they can work effectively as charge transporting materials in combination with the charge generating material 3 which absorbs the light in the visible region and generates charge carriers.

In the photoconductor as shown in FIG. 3, there is formed on the electroconductive support 1 a two-layered photoconductive layer 2b comprising a charge generation layer 5 consisting essentially of the charge generating material 3 and a charge transport layer 4 containing a benzylideneindene compound according to the present invention.

In this photoconductor, light which has passed through the charge transport layer 4 reaches the charge generation layer 5, and charge carriers are generated within the charge generation layer 5. The charge carriers which are necessary for the light decay for latent electrostatic image formation are generated by the charge generating material 3, accepted and transported by the charge transport layer 4. In the charge transport layer 4, the benzylideneindene compound mainly works for transporting the charge carriers. The generation and transportation of the charge carriers are performed by the same mechanism as that in the photoconductor shown in FIG. 2.

When an electrophotographic photoconductor according to the present invention as shown in FIG. 1 is prepared, at least one benzylideneindene compound having the previously described formula (I) is dissolved in a binder resin solution, and a sensitizing dye is then added to the above prepared mixture, so that a photoconductive layer coating liquid is prepared. The thus prepared photoconductive layer coating liquid is coated on an electroconductive support 1 and dried, so that a photoconductive layer 2 is formed on the electroconductive support 1.

It is preferable that the thickness of the photoconductive layer 2 be in the range of 3 to 50 μm, more preferably in the range of 5 to 20 μm. It is preferable that the amount of the benzylideneindene compound contained in the photoconductive layer be in the range of 30 to 70 wt. %, more preferably about 50 wt. % of the total weight of the photoconductive layer 2. Furthermore, it is preferable that the amount of the sensitizing dye contained in the photoconductive layer 2 be in the range of 0.1 to 5 wt. %, more preferably in the range of 0.5 to 3 wt. % of the total weight of the photoconductive layer 2.

Specific examples of the sensitizing dye for use in the present invention are: triarylmethane dyes such as Brilliant Green, Victoria Blue B, Methyl Violet, Crystal Violet and Acid Violet 6B; xanthene dyes such as Rhodamine B, Rhodamine 6G, Rhodamine G Extra, Eosin S, Erythrosin, Rose Bengale and Fluoresceine; thiazine dyes such as Methylene Blue; cyanine dyes such as cyanin; and pyrylium dyes such as 2,6-diphenyl-4-(N,N-dimethylaminophenyl)thiapyrylium perchlorate and benzopyrylium salts (Japanese Patent Publication 48-25658). These sensitizing dyes can be used alone or in combination.

An electrophotographic photoconductor according to the present invention as shown in FIG. 2 can be prepared, for example, by the following method. A charge generating material 3 in the form of finely-divided particles is dispersed in a solution in which one or more benzylideneindene compounds according to the present invention and a binder agent are dispersed. The thus prepared dispersion is coated on the electroconductive support 1 and then dried, whereby a photoconductive layer 2a is formed on the electroconductive support 1.

It is preferable that the thickness of the photoconductive layer 2a be in the range of 3 to 50 μm, more preferably in the range of 5 to 20 μm. It is preferable that the amount of the benzylideneindene compound contained in the photoconductive layer 2a be in the range of 10 to 95 wt. %, more preferably in the range of 30 to 90 wt. % of the total weight of the photoconductive layer 2. Furthermore, it is preferable that the amount of the charge generating material 3 contained in the photoconductive layer 2a be in the range of 0.1 to 50 wt. %, more preferably in the range of 1 to 20 wt. % of the total weight of the photoconductive layer 2a.

Specific examples of the charge generating material 3 are as follows: inorganic pigments such as selenium, a selenium-tellurium alloy, cadmium sulfide, a cadmium sulfide-selenium alloy and α-silicon; and organic pigments, for example, C.I. Pigment Blue 25 (C.I. 21180), C.I. Pigment Red 41 (C.I. 21200), C.I. Acid Red 52 (C.I. 45100), and C.I. Basic Red 3 (C.I. 45210); an azo pigment having a carbazole skeleton (Japanese Laid-Open Patent Application 53-95033), an azo pigment having a distyryl benzene skeleton (Japanese Laid-Open Patent Application 53-133455), an azo pigment having a triphenylamine skeleton (Japanese Laid-Open Patent Application 53-132347), an azo pigment having a dibenzothiophene skeleton (Japanese Laid-Open Patent Application 54-217287), an azo pigment having an oxadiazole skeleton (Japanese Laid-Open Patent Application 54-12742), an azo pigment having a fluorenone skeleton (Japanese Laid-Open Patent Application 54-22834), an azo pigment having a bisstilbene skeleton (Japanese Laid-Open Patent Application 54-17733), an azo pigment having a distyryl oxadiazole skeleton (Japanese Laid-Open Patent Application 54-2129), and an azo pigment having a distyryl carbazole skeleton (Japanese Laid-Open Patent Application 54-14967); a phthalocyanine pigment such as C.I. Pigment Blue 16 (C.I. 74100); indigo pigments such as C.I. Vat Brown 5 (C.I. 73410) and C.I. Vat Dye (C.I. 73030); and perylene pigments such as Algol Scarlet B and Indanthrene Scarlet R (made by Bayer Co., Ltd.). These charge generating materials can be used alone or in combination.

An electrophotographic photoconductor according to the present invention as shown in FIG. 3 can be prepared, for example, by the following method. A charge generating material 3 is vacuum-evaporated on the electroconductive support 1, whereby a charge generation layer 5 is formed. Alternatively, a charge generating material 3 in the form of finely-divided particles is dispersed in a solution of a binder agent, and this dispersion is applied to the electroconductive support 1 and then dried. If necessary, the applied layer is subjected to buffing to make the surface smooth or to adjust the thickness of the layer to a predetermined thickness, whereby a charge generation layer 5 is formed. A charge transport layer 4 is then formed on the above-prepared charge generation layer 5 by applying a solution of one or more benzylideneindene compounds and a binder agent to the charge generation layer 5 and then drying the applied solution. The charge generating material employed in this photoconductor is the same as that employed in the photoconductor shown in FIG. 2.

It is preferable that the thickness of the charge generation layer 5 be 5 μm or less more preferably 2 μm or less. It is preferable that the thickness of the charge transport layer 4 be in the range of 3 to 50 μm, more preferably in the range of 5 to 20 μm.

In the case where the charge generation layer 5 is prepared by coating the dispersion in which finely-divided particles of a charge generating material 3 are dispersed in a binder agent on the electroconductive support 1, it is preferable that the amount of the charge generating material 3 in the charge generation layer 5 be in the range of 10 to 95 wt. %, more preferably in the range of about 50 to 90 wt. % of the entire weight of the charge generation layer 5. Furthermore, it is preferable that the amount of the benzylideneindene compound contained in the charge transport layer 4 be in the range of 10 to 95 wt. %, more preferably in the range of 30 to 90 wt. % of the entire weight of the charge transport layer 4.

As the electroconductive support 1 for use in the present invention, a metal plate or metal foil, for example, made of aluminum, a plastic film on which a metal, for example, aluminum is evaporated, or paper which has been treated so as to be electroconductive, can be employed.

Specific examples of the binder agent for use in the present invention are condensation resins such as polyamide, polyurethane, polyester, epoxy resin, polyketone and polycarbonate; and resins having an adhesive force such as polyvinylketone, polystyrene, poly-N-vinylcarbazole and polyacrylamide.

When necessary, there can be added to the binder agent a plasticizer, for example, halogenated paraffin, polybiphenyl chloride, dimethylnaphthalene and dibutyl phthalate.

In the above-described photoconductors according to the present invention, if necessary, an adhesive or barrier layer can be interposed between the electroconductive support and the photoconductive layer. The adhesive layer or the barrier layer can be made of, for example, polyamide, nitrocellulose, or aluminum oxide. It is preferable that the thickness of the adhesive layer or barrier layer be 1 μm or less.

When copying is performed by use of the photoconductors according to the present invention, the surface of the photoconductor is charged uniformly in the dark to a predetermined polarity. The uniformly charged photoconductor is exposed to a light image so that a latent electrostatic image is formed on the photoconductor. The thus formed latent electrostatic image is developed by a developer to a visible image, and when necessary, the developed image can be transferred to a sheet of paper. The photoconductors according to the present invention have high photosensitivity and excellent flexibility.

Preparation of embodiments of an electrophotographic photoconductor according to the present invention will now be explained in detail by referring to the following examples.

EXAMPLE P-1

The following components were ground and dispersed in a ball mill to prepare a charge generation layer coating liquid:

| | Parts by Weight |
|---|---|
| Diane Blue (C.I. Pigment Blue 25, C.I. 21180) (Charge generating material of the formula in Table 4) | 76 |
| 2% tetrahydrofuran solution of a polyester resin (Trademark "Vylon 200" made by Toyobo Co., Ltd.) | 260 |
| Tetrahydrofuran | 3,700 |

This charge generation layer coating liquid was coated by a doctor blade on the aluminum-deposited surface of an aluminum-deposited polyester base film, which served as an electroconductive support, so that a charge generation layer was formed on the electroconductive support with a thickness of about 1 μm when dried at room temperature.

Then the following components were mixed and dissolved, so that a charge transport layer coating liquid was prepared:

| | Parts by Weight |
|---|---|
| Benzylideneindene-compound No. 22-1 (prepared in Synthesis Example 1) | 2 |
| Polycarbonate resin (Trademark "Panlite K 130011 made by Teijin Limited.) | 2 |
| Tetrahydrofuran | 16 |

The thus prepared charge transport layer coating liquid was coated on the aforementioned charge generation layer by a doctor blade and dried at 80° C. for 2 minutes and then at 105° C. for 5 minutes, so that a charge transport layer with a thickness of about 20 μm was formed on the charge generation layer. Thus, an electrophotographic photoconductor No. 1 according to the present invention was prepared.

EXAMPLES P-2 TO P-4

Example 1 was repeated except that the charge generating material and the benzylideneindene compound working as the charge transporting material employed in Example 1 were respectively replaced by the charge generating materials and the benzylideneindene compounds as listed in Table 4, whereby electrophotographic photoconductors No. 2 to No. 41 according to the present invention were prepared.

TABLE 4

| Photoconductor No. | Charge Generating Material | Charge Transporting Material Benzylideneindene Compound No. |
|---|---|---|
| 1 | ⟨○⟩—HNOC  OH  H₃CO       OCH₃  HO  CONH—⟨○⟩<br>         ⟨○⟩—N=N—⟨○⟩—⟨○⟩—N=N—⟨○⟩ | 22 |

TABLE 4-continued

| Photo-conductor No. | Charge Generating Material | Charge Transporting Material Benzylideneindene Compound No. |
|---|---|---|
| 2 | [structure: bis-azo compound with two Cl substituents on central biphenyl, flanked by hydroxynaphthalene carboxanilide groups] | 22 |
| 3 | [structure: azo compound with 2,4-dimethylphenyl carboxamide, hydroxynaphthalene, -N=N-C6H4-CH=CH-C6H4-CH=* and second half with *CH-C6H4-N=N- hydroxynaphthalene CONH-2,4-dimethylphenyl] (hereinafter referred to as P-1) | 22 |
| 4 | [structure: bis-azo compound with central 1,3,4-oxadiazole linked to two phenyl-azo-hydroxynaphthalene carboxanilide groups] | 22 |
| 5 | [structure: bis-azo fluorenone with two (2-chlorophenyl)carbamoyl hydroxynaphthalene groups] (hereinafter referred to as P-2) | 22 |
| 6 | [structure: tris-azo compound with central triphenylamine, three hydroxynaphthalene CONH-C6H4-OCH3 groups] | 22 |
| 7 | β-type Copper Phthalocyanine | 22 |
| 8 | [structure: bis-azo compound with two OCH3 substituents on central biphenyl, flanked by hydroxynaphthalene carboxanilide groups] | 20 |

TABLE 4-continued

| Photo-conductor No. | Charge Generating Material | Charge Transporting Material Benzylideneindene Compound No. |
|---|---|---|
| 9 | (structure: bis-azo compound with phenyl-HNOC, OH, Cl, naphthol groups) | 20 |
| 10 | P-1 | 20 |
| 11 | P-2 | 20 |
| 12 | P-1 | 12 |
| 13 | P-2 | 12 |
| 14 | P-1 | 10 |
| 15 | P-2 | 10 |
| 16 | P-1 | 33 |
| 17 | P-2 | 33 |
| 18 | P-1 | 55 |
| 19 | P-2 | 55 |
| 20 | P-1 | 2 |
| 21 | P-2 | 2 |
| 22 | P-1 | 24 |
| 23 | P-2 | 24 |
| 24 | P-1 | 25 |
| 25 | P-2 | 25 |
| 26 | P-1 | 27 |
| 27 | P-2 | 27 |
| 28 | P-1 | 48 |
| 29 | P-2 | 48 |
| 30 | P-1 | 63 |
| 31 | P-2 | 63 |
| 32 | P-1 | 73 |
| 33 | P-2 | 73 |
| 34 | P-1 | 9 |
| 35 | P-2 | 9 |
| 36 | P-1 | 23 |
| 37 | P-2 | 23 |
| 38 | P-1 | 84 |
| 39 | P-2 | 84 |
| 40 | P-1 | 85 |
| 41 | P-2 | 85 |

EXAMPLE P-42

Selenium was vacuum-deposited with a thickness of about 1.0 μm on an about 300 μm thick aluminum plate so that a charge generation layer was formed on the aluminum plate.

A charge transport layer coating liquid was prepared by mixing and dispersing the following components:

| | Parts by Weight |
|---|---|
| Benzylideneindene compound No. 22-1 in Table 1 | 2 |
| Polyester resin (Trademark "Polyester Adhesive 49000" made by Du Pont Co.) | 3 |
| Tetrahydrofuran | 45 |

The thus prepared charge transport layer coating liquid was coated on the above-prepared selenium-deposited charge generation layer by a doctor blade, dried at room temperature and further dried under reduced pressure, so that a charge transport layer with a thickness of about 10 μm was formed on the charge generation layer. Thus an electrophotographic photoconductor No. 42 according to the present invention was prepared.

EXAMPLE P-43

Example 42 was repeated except that selenium-deposited charge generation layer with a thickness of about 1.0 μm was replaced by a charge generation layer comprising a perylene pigment having the following formula with a thickness of about 0.3 μm, and the benzylideneindene compound No. 22-1 in the formulation of the charge transport layer coating liquid employed in Example 42 was replaced by benzylideneindene compound No. 20 in Table 1, whereby an electrophotographic photoconductor No. 43 was prepared.

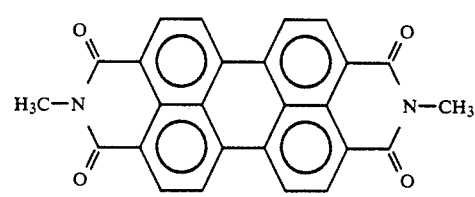

EXAMPLE p-44

A mixture of 1 part by weight of Diane Blue (the same as employed in Example 1) and 158 parts by weight of tetrahydrofuran was ground and dispersed in a ball mill. To this mixture, 12 parts by weight of the benzylideneindene compound No. 22 and 18 parts by weight of a polyester resin (Trademark "Polyester Adhesive 49000" made by Du Pont Co.) were added and mixed, whereby a photoconductive layer coating liquid was prepared.

The thus prepared photoconductive layer coating liquid was coated on an aluminum-deposited polyester film by a doctor blade and dried at 100° C. for 30 minutes, so that a photoconductive layer with a thickness of about 16 μm was formed on the aluminum-deposited polyester film. Thus an electrophotographic photoconductor No. 44 according to the present invention was prepared.

The thus prepared electrophotographic photoconductors No. 1 to No. 44 were charged negatively or positively in the dark under application of −6 kV or +6 kV of corona charge for 20 seconds and then allowed to stand in the dark for 20 seconds without applying any charge thereto. At this moment, the surface potential $V_{po}(V)$ of each photoconductor was measured by a Paper Analyzer (Kawaguchi Electro Works, Model SP-428). Each photoconductor was then illuminated by a tungsten lamp in such a manner that the illuminance on the illuminated surface of the photoconductor was 20 lux, so that the exposure $E_{\frac{1}{2}}$ (lux.seconds) required to reduce the initial surface potential $V_{po}(V)$ to $\frac{1}{2}$ the initial surface potential $V_{po}(V)$ was measured. The results are shown in Table 5.

TABLE 5

| Example No. | $V_{po}$ (V) | $E_{1/2}$ (lux · second) |
| --- | --- | --- |
| 1 | −1380 | 2.90 |
| 2 | −1140 | 2.00 |
| 3 | −1298 | 1.30 |
| 4 | −1350 | 3.80 |
| 5 | −1144 | 1.10 |
| 6 | −1100 | 1.30 |
| 7 | −1020 | 2.60 |
| 8 | −1280 | 3.00 |
| 9 | −1100 | 2.50 |
| 10 | −1248 | 1.40 |
| 11 | −1283 | 1.30 |
| 12 | −1472 | 1.50 |
| 13 | −1158 | 1.60 |
| 14 | −1354 | 1.90 |
| 15 | −1150 | 1.50 |
| 16 | −1140 | 1.40 |
| 17 | −970 | 0.90 |
| 18 | −1100 | 1.40 |
| 19 | −1020 | 0.90 |
| 20 | −1467 | 1.50 |
| 21 | −1332 | 1.60 |
| 22 | −1250 | 1.20 |
| 23 | −490 | 0.60 |
| 24 | −1100 | 1.10 |
| 25 | −1090 | 1.00 |
| 26 | −1200 | 1.10 |
| 27 | −1120 | 1.00 |
| 28 | −1220 | 1.70 |
| 29 | −1010 | 1.40 |
| 30 | −1340 | 1.20 |
| 31 | −1190 | 1.20 |

TABLE 5-continued

| Example No. | $V_{po}$ (V) | $E_{1/2}$ (lux · second) |
| --- | --- | --- |
| 32 | −990 | 1.80 |
| 33 | −1210 | 1.30 |
| 34 | −1370 | 1.37 |
| 35 | −1090 | 1.20 |
| 36 | −1240 | 1.27 |
| 37 | −940 | 0.90 |
| 38 | −1200 | 1.18 |
| 39 | −1070 | 1.00 |
| 40 | −1370 | 1.29 |
| 41 | −1150 | 1.40 |
| 42 | −1110 | 2.40 |
| 43 | −1150 | 3.80 |
| 44 | +960 | 2.30 |

Each of the above electrophotographic photoconductors No. 1 through No. 44 was incorporated in a commercially available electrophotographic copying machine and a latent electrostatic image was formed thereon by being exposed to a light image. The latent electrostatic image was developed with a dry type developer to a visible toner image, electrostatically transferred to a transfer sheet made of plain paper and fixed thereto. As a result, a clear transferred image was obtained by each of the photoconductors. When a liquid developer was employed instead of the dry type developer, clear transfer images were obtained likewise.

According to the present invention, the chargeability and photosensitivity of the electrophotographic photoconductors comprising an electroconductive support and a photoconductive layer formed thereon which comprises at least one benzylideneindene compound having the formula (I) are superior to conventional photoconductors. Furthermore, the above electrophotographic photoconductors according to the present invention are capable of yielding clear images.

What is claimed is:

1. Benzylideneindene compounds having formula (I-1):

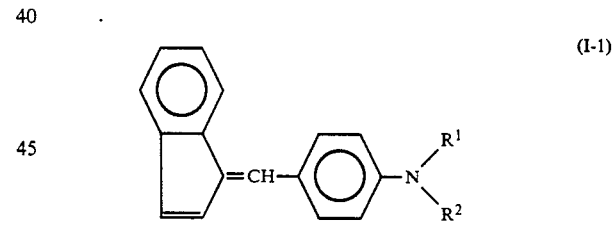

wherein $R^1$ and $R^2$ each represent a phenyl group which may have a substituent, a benzyl group which may have a substituent, or a biphenylyl group.

2. The benzylideneindene compounds as claimed in claim 1, wherein the substituent of said benzyl group is an alkyl group having 1 to 4 carbon atoms.

3. The benzylideneindene compounds as claimed in claim 1, wherein the substituent of said phenyl group is selected from the group consisting of an alkyl group having 1 to 4 carbon atoms, an alkoxyl group having 1 to 4 carbon atoms, and a halogen.

* * * * *

UNITED STATES PATENT AND TRADEMARK OFFICE
CERTIFICATE OF CORRECTION

PATENT NO. : 5,250,733
DATED : October 5, 1993
INVENTOR(S) : Aruga, et. al.

It is certified that error appears in the above-indentified patent and that said Letters Patent is hereby corrected as shown below:

COLUMN 1, LINE 23, "exposed t", shoud read --exposed to--.

COLUMN 4, LINE 14, "formula I)" should read --formula (I)--.

COLUMN 20, LINE 62, "amino[benzaldehyde" should read --amino]benzaldehyde--.

COLUMN 28, LINE 11, under Parts by Weight, "260" should read --1260--;

LINE 32, "Panlite K 130011" should read --Panlite K 1300"--.

Signed and Sealed this

Third Day of January, 1995

Attest:

BRUCE LEHMAN

Attesting Officer      Commissioner of Patents and Trademarks